United States Patent [19]

Salzman et al.

[11] Patent Number: 4,796,995
[45] Date of Patent: Jan. 10, 1989

[54] OPTICALLY ACTIVE BIOLOGICAL PARTICLE DISTINGUISHING APPARATUS

[75] Inventors: Gary C. Salzman, Los Alamos, N. Mex.; Robert H. Kupperman, Washington, D.C.

[73] Assignee: The United States Department of Energy, Washington, D.C.

[21] Appl. No.: 93,052

[22] Filed: Sep. 2, 1987

Related U.S. Application Data

[63] Continuation of Ser. No. 815,185, Dec. 23, 1985, abandoned, which is a continuation of Ser. No. 763,894, Aug. 9, 1985, abandoned, which is a continuation of Ser. No. 452,360, Dec. 22, 1982, abandoned.

[51] Int. Cl.[4] .............................................. G01N 21/21
[52] U.S. Cl. ..................................... 356/368; 356/338
[58] Field of Search ............... 356/336, 338, 339, 341, 356/342, 364, 365, 367, 368, 369; 250/225

[56] References Cited

U.S. PATENT DOCUMENTS

| | | |
|---|---|---|
| 3,600,094 | 8/1971 | Liskowitz . |
| 3,785,735 | 1/1974 | Friedman et al. ............... 356/342 X |
| 3,817,634 | 6/1974 | Barron et al. . |
| 3,924,180 | 12/1975 | Salzman et al. . |
| 4,140,902 | 2/1979 | Young .............................. 356/339 X |
| 4,200,802 | 4/1980 | Salzman et al. . |
| 4,224,567 | 9/1980 | Hoffman . |
| 4,306,809 | 12/1981 | Azzam ................................. 356/368 |

OTHER PUBLICATIONS

Thompson, "Measurement of Polarized Light Interactions via the Mudler Matrix," *Applied Optics* vol. 19, No. 8, pp. 1323–1332, 4/80.
Hunt et al. "A New Polarization-Modulated Light Scattering Instrument," *Rev. Sci. Instr.*, vol. 44, No. 12, pp. 1753–1762, 12/73.
Bickel et al., "Polarized Light Scattering from Biological Systems: A Technique for Cell Differentiation," *J. Biol. Phys.*, V. 9, pp. 53–66, 1981.
Bickel et al. "Application of Polarization Effects in Light Scattering: A New Biophysical Tool," *Proc. Nat. Acad. Sci. USA*, v. 73, No. 2, pp. 486–490, 2/76.

*Primary Examiner*—Davis L. Willis
*Assistant Examiner*—Matthew W. Koren
*Attorney, Agent, or Firm*—Samuel M. Freund; Paul D. Gaetjens; Judson R. Hightower

[57] ABSTRACT

The disclosure is directed to organic particle sorting and identification. High frequency pulses of circularly polarized light, alternating between left and right, intersect a fast moving stream of organic particles. Circular intensity differential scattering and linear intensity differential scattering are monitored to uniquely identify a variety of organic particles.

18 Claims, 1 Drawing Sheet

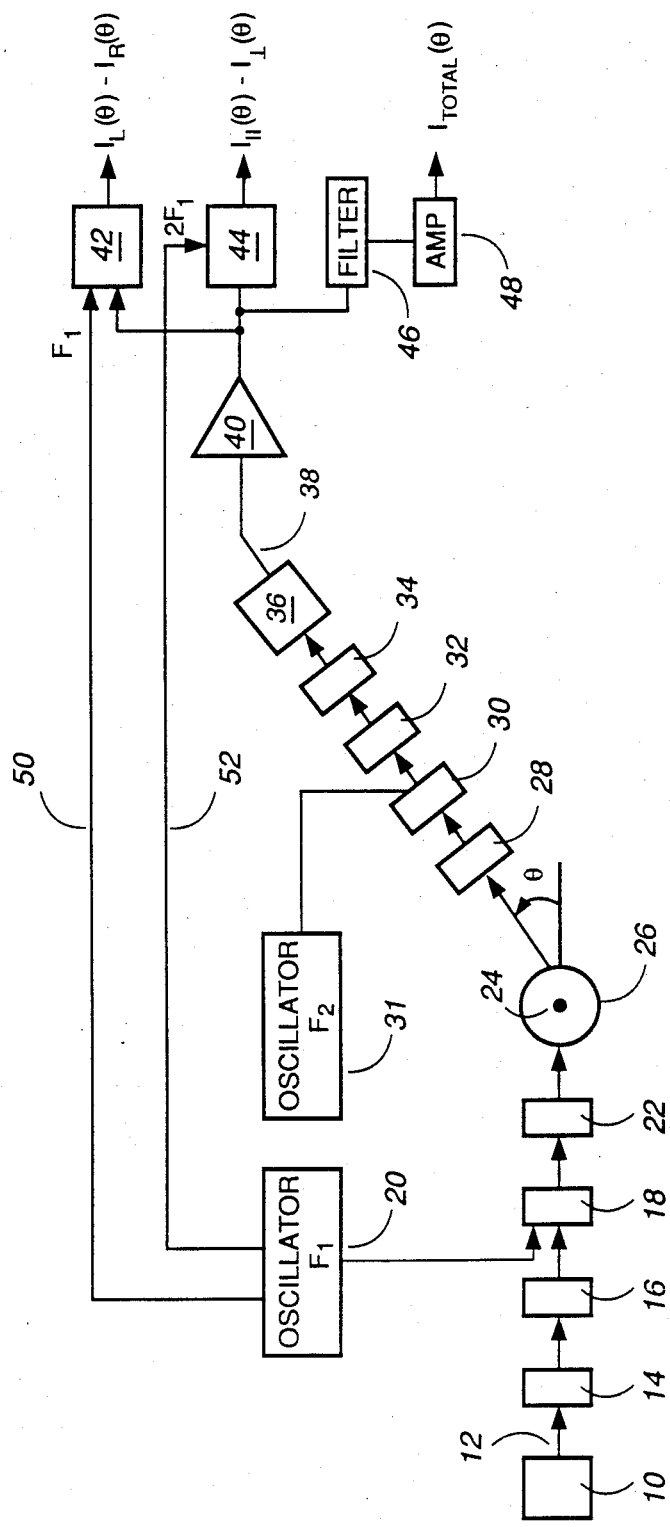
*Figure*

OPTICALLY ACTIVE BIOLOGICAL PARTICLE DISTINGUISHING APPARATUS

This invention is the result of a contract with the Department of Energy (contract No. W-7405-ENG-36).

This is a continuation of application Ser. No. 815,185 filed Dec. 23, 1985 now abandoned which is a continuation of application Ser. No. 763,894 filed Aug. 9, 1985 now abandoned which is a continuation of application Ser. No. 452,360 filed Dec. 22, 1982 now abandoned.

BACKGROUND OF THE INVENTION

The field of the invention relates to organic particle sorting and identification and more particularly to identifying and distinguishing organic particles such as microorganisms, viruses, pollen and eukaryotic cell types.

Cell sorting is a well established field and includes electrical cell analyzing devices such as disclosed in U.S. Pat. Nos. 3,924,180 and 3,946,239 to Salzman et al. and U.S. Pat. No. 4,224,567 to Hoffman. While these devices are able to discern certain characteristics about cells, they are unable to determine differences in the long range order of the genetic material among different cell types.

Some experimenters have looked at cells in suspension. Two publications, Thompson, Bottiger and Fry (Applied Optics 19, 1323 (1980)) and Hunt and Huffman, (Rev. Sci. Instrument 44 1753 (1973)) disclose experiments on cells in suspension using polarized light. The devices used in such experiments are limited to looking at a group of cells in suspension, such as $10^8$ viruses. Too, their light sources have only been cycled by Pockels cells driven by alternating high voltage at low frequencies, at 100 kHz maximum.

In practicing the invention, optical modulators are driven at high frequencies on the order of 40 mHz. Such high frequencies are needed to obtain information from fast moving (10 meters per second) single cells in a cell stream. A low frequency source such as of the aforementioned experiments produces too long a pulse to obtain information from a fast moving cell because the cell would not be present during the full duration of the pulse. In practicing the invention, due to rapid light cycling, fast moving cells can be analyzed one at a time and the cells can be of a variety of types whereas the Thompson et al. and Hunt et al. devices are limited to the study of suspensions of a single strain of cells.

One object of the invention is to uniquely identify a variety of bacteria, viruses, pollens and eukaryotic cells.

Another object of the present invention is to distinguish cells or organic particles in a cell stream utilizing circular intensity differential scattering and linear intensity differential scattering from the cells.

One advantage of the invention is that no staining or fixation of cells is required.

Another advantage of the instant invention is that live cells can be analyzed and sorted.

SUMMARY OF THE INVENTION

In accordance with the invention, there is provided an apparatus for identifying and distinguishing organic particles in a cell stream comprising structure for producing from a continuous beam of light left and right circularly polarized components and for optically modulating the components at a first frequency. The polarized modulated components pass through a stream containing the organic particles to be identified or distinguished. Light from the components scattered and amplitude modulated by the particles is then further polarized and optically modulated at a second frequency which differs from the first frequency. The further polarized and optically amplitude modulated scattered light is received and analyzed in order to identify or distinguish the organic particles in the stream.

BRIEF DESCRIPTION OF THE DRAWINGS

The accompanying drawing, which is incorporated in and forms a part of the specification, illustrates a preferred embodiment of the present invention and, together with the description, serves to explain the principles of the invention. In the drawing:

The FIGURE is a schematic showing of a preferred embodiment of the invention.

DESCRIPTION OF THE PREFERRED EMBODIMENT

Reference is now made to the Figure which shows a preferred embodiment of the invention comprising a light source 10 which may be, for example, a continuous wave laser operating in the ultraviolet, visible, or infrared portion of the spectrum. A beam 12 produced by laser 10 passes through a beam expander 14 which comprises standard optics well known to those skilled in the art. The expanded beam passes through a polarizer 16 which in the preferred embodiment comprises a prism polarizer having its passing axis set at 90° to the horizontal plane of the drawing. Alternatively, the polarizer 16 may have its passing axis disposed at a positive 45° to the horizontal plane.

Polarizer 16 selects the vertical linearly polarized component in the incident beam. The polarized beam then passes through an optical modulator 18 preferably set at an angle of +45° to the horizontal plane. Modulator 18 may be a Pockels Cell driven up to about 40 MHz by, for example, an oscillator 20 operated at a first frequency $F_1$ near about 40 MHz. Optical modulator 18 converts the linearly polarized beam into oscillating left and right circular polarized components at the frequency $F_1$. A second or alternative orientation for optical modulator 18 is at 0° with respect to the reference horizontal plane.

From modulator 18 the circularly polarized components of the beam pass through focusing and beam shaping optics 22 which are well known to those skilled in the art. Optics 22 focus the beam on a cell stream 24 passing through a flow chamber 26 which may be one such as described in U.S. Pat. Nos. 4,200,802 or 4,224,567. The cell stream may be, for example, 10 μm in diameter and may contain bacteria, viruses, microorganisms and/or eukaryotic cells, all of which pass in single file. The focused beam intersects a stream of organic particles in the cell stream 24. The beam components are amplitude modulated and scattered at an angle by each cell as it passes through the flow chamber θ. Amplitude modulation is proportional to the circular birefringence of a cell at the frequency $F_1$ and is proportional to the linear birefringence of the cell at a frequency of twice $F_1$ ($2F_1$).

Collection optics 28 collect the scattered light components. It will be appreciated that such optics are only schematically shown herein and may be disposed substantially about the flow chamber 26. Collection optics 28 pass the components to a second optical modulator 30, preferably set at an angle of +45° to the horizontal reference plane. Modulator 30 operates at a second frequency $F_2$ which is different from $F_1$. An alternative orientation for optical modulator 30 is with its fast axis parallel to the horizontal reference plane. An oscillator 31 supplies frequency $F_2$ to optical modulator 30.

The scattered beam components then pass through a second polarizer 32, preferably a prism polarizer set at an angle of 90° to the horizontal reference plane. Alternatively its orientation may be at −45° to the horizontal reference plane. The beam components are then focused onto a spatial filter 34, such as a pinhole and pass therethrough to impinge on the face of a photodetector 36 such as a photomultiplier tube which produces an output signal on a line 38. A preamplifier 40 amplifies the output signal. Two phase sensitive detectors 42 and 44 extract the amplitude modulated components at frequencies $F_1$ and $F_2$ from the amplified output signal. A filter-amplifier combination 46 and 48 detects an envelope signal proportional to the total amount of scattered light at angle $\theta$. Oscillator 20 supplies frequency $2F_1$ to phase sensitive detectors 42 and 44 through lines 50 and 52 respectively.

The circular intensity differential scattering is given by $$CIDS(\theta) = \frac{I_L(\theta) - I_R(\theta)}{I_{TOTAL}(\theta)}$$

where $I_L(\theta)$=the amount of light scattered into 74 when the incident beam is left circularly polarized, $I_R(\theta)$=the amount of light scattered into $\theta$ when the incident beam is right circularly polarized, and $I_{TOTAL}(\theta) = I_L(\theta) + I_R(\theta)$ = total amount of light scattered into $\theta$.

The linear intensity differential scattering is given by $$POL(\theta) = \frac{I_\parallel(\theta) - I_\perp(\theta)}{I_{TOTAL}(\theta)}$$

where $I_\parallel(\theta)$=the amount of light scattered when the incident beam is linearly polarized, parallel to the scattering plane, $I_\perp(\theta)$=the amount of light scattered when the incident beam is polarized perpendicular to the scattering plane, and $I_{TOTAL}(\theta) = I_\parallel(\theta) + I_\perp(\theta) = I_L(\theta) + I_R(\theta)$ = total amount of light scattered.

The two signals $CIDS(\theta)$ and $POL(\theta)$ can be used separately or in combination to uniquely identify a variety of organic particles such as bacteria, viruses, pollen, and eukaryotic cells. No staining or fixation is required and live cells can be analyzed and sorted. Each type of organic particle can be determined or identified by its unique $CIDS(\theta)$ and $POL(\theta)$ signature. In practicing the invention, a plurality of scattered light analyzers and photodetectors may be disposed at various angles with respect to the direction of the beam, although for purposes of illustration only one scattered light analyzer photodetector is shown.

The scattering plane is defined by a ray along the incident light beam and a ray from the object to the detector.

The foregoing description of the preferred embodiment of the invention has been presented for purposes of illustration and description. It is not intended to be exhaustive or to limit the invention to the precise form disclosed, and obviously many modifications and variations are possible in light of the above teaching. The embodiment was chosen and described in order to best explain the principles of the invention and its practical application to thereby enable others skilled in the art to best utilize the invention in various embodiments and with various modifications as are suited to the particular use contemplated. It is intended that the scope of the invention be defined by the claims appended hereto.

What is claimed is:

1. An apparatus for distinguishing microorganisms, pollens, and eukaryotic cell types as single cells in a cell stream, said apparatus comprising:

a source for a continuous light beam of suitable diameter in the infrared to ultraviolet light range;

means for selecting a linearly polarized component from the beam;

first means for optically modulating the linearly polarized component of the beam into left and right circularly polarized components at a single first frequency;

means for shaping the circularly polarized components and for focusing on and passing the left and right circularly polarized components through a flow chamber through which a stream containing the cells to be distinguished can be flowed as individual cells;

means for collecting the circularly polarized components scattered by a cell to be distinguished at least one angle relative to the direction of the continuous light beam, the scattered components being amplitude modulated at said first frequency in accordance with the circular birefringence of the cell and amplitude modulated in accordance with the linear birefringence of the cell at a second frequency, said second frequency being twice said first frequency;

second means for optically modulating the collected scattered beam components at a single third frequency;

means for again linearly and circularly polarizing the modulated scattered beam components;

means for spatially filtering said again polarized modulated scattered beam components;

photodetector means for receiving said spatially filtered amplitude modulated scattered beam components and for generating an output in accordance therewith; and means for receiving and analyzing the output and for extracting the amplitude modulated components at at most said first frequency and said second frequency at said at least one angle relative to the direction of the continuous light beam to identify microorganisms and eukaryotic cells as individual cells in the cell stream.

2. The invention of claim 1 wherein said polarized component selecting means comprises a prism polarizer.

3. The invention of claim 2 wherein the passing axis of said prism polarizer is set at about 90° to the beam.

4. The invention of claim 2 wherein the passing axis of said prism polarizer is set at about 45° to the beam.

5. The invention of claim 1 wherein said first optically modulating means comprises a Pockels Cell driven at said first frequency which is up to about 40 MHz.

6. The invention of claim 1 wherein the passing axis of said first optical modulating means is set at about 45° to the beam.

7. The invention of claim 1 wherein the passing axis of said first optically modulating means is set at about 0° to the beam.

8. The invention of claim 1 wherein the passing axis of said second optically modulating means is set at about 45° to the beam.

9. The invention of claim 1 wherein the passing axis of said second optically modulating means is set about parallel to the beam.

10. The invention of claim 9 wherein said means for again polarizing comprises a prism polarizer set at about 90° to the beam.

11. The invention of claim 9 wherein said means for again polarizing comprises a prism polarizer set at about −45° to the beam.

12. The invention of claim 1 wherein said photodetector means comprises at least one photomultiplier tube.

13. The invention of claim 1 wherein said receiving and analyzing means comprises at least one pair of phase sensitive detectors for extracting the amplitude modulated first and second frequency components.

14. The invention of claim 1 wherein said receiving and analyzing means comprises at least one filter-amplifier combination for detecting an envelope signal proportional to the total amount of scattered light at at least one selected angle to the beam.

15. The invention of claim 1 wherein said receiving end analyzing means comprises means for determining the circular intensity differential scattering which is identified by $$CIDS(\theta) = \frac{I_L(\theta) - I_R(\theta)}{I_{TOTAL}(\theta)}$$

where $CIDS(\theta)$ is the circular intensity differential scattering, $I_L(\theta)$ is the amount of light scattered into $\theta$ when the incident beam is left circularly polarized, $I_R(\theta)$ is the amount of light scattered into $\theta$ when the incident beam is right circularly polarized and $I_{TOTAL}(\theta)$ is $I_L(\theta)+I_R(\theta)$.

16. The invention of claim 1 wherein said receiving end analyzing means comprises means for determining the linear intensity differential scattering which is given by $$POL(\theta) = \frac{I_{\parallel}(\theta) - I_{\perp}(\theta)}{I_{TOTAL}(\theta)}$$

where $POL(\theta)$ is the linear intensity differential scattering, $I_{\parallel}(\theta)$ is the amount of light scattered when the incident beam is linearly polarized parallel to the scattering plane, $I_{\perp}(\theta)$ is the amount of light scattered when the incident beam is polarized perpendicular to the scattering plane and $I_{TOTAL}(\theta)$ is $I_{\parallel}(\theta)+I_{\perp}(\theta)$.

17. An apparatus for distinguishing microorganisms, pollen and eukaryotic cell types as individual cells comprising:
means for producing a continuous beam of light of a selected size in the infrared to ultraviolet range;
means for optically amplitude modulating at a single first frequency and circularly polarizing the beam and for passing the beam through a cell stream of individual cells, said means for optically amplitude modulating and circularly polarizing comprising a first optical modulator operating at a single first frequency;
means for further amplitude modulating and polarizing the cell scattered light at at least one angle relative to the direction of the continuous beam of light, said means for further amplitude modulating and polarizing comprising at least one second optical modulator operating at a single second frequency different from the first frequency; and
means for receiving and analyzing the further modulated and polarized cell scattered light, said means for receiving and analyzing comprising means for simultaneously processing amplitude modulated components of cell-scattered light at at least one angle relative to the direction of the continuous beam of light at the single first frequency and at a frequency twice that of the first frequency in order to identify the microorganisms, pollen, and eukaryotic cell types as individual cells in the cell stream.

18. An apparatus for categorizing individual organic particles in a particle stream comprising:
means for producing left and right circularly polarized components of a continuous light beam optically amplitude modulated at a single first frequency;
means for passing the components through a particle stream containing individual particles;
means for further polarizing and optically amplitude modulating at a single third and different frequency the components as scattered by individual particles in the stream at at least one angle relative to the direction of the continuous light beam; and
means for receiving and analyzing the further polarized and modulated components solely at the first frequency and at twice the first frequency in order to categorize the individual particles in the particle stream.

* * * * *